United States Patent [19]

Pirie et al.

[11] Patent Number: 4,468,351

[45] Date of Patent: Aug. 28, 1984

[54] PROCESS FOR DEBROMINATION OF DIBROMOPENICILLANIC ACID AND DERIVATIVES

[75] Inventors: Donald K. Pirie, Uncasville; Paul D. Weeks, Gales Ferry, both of Conn.

[73] Assignee: Pfizer Inc., New York, N.Y.

[21] Appl. No.: 501,731

[22] Filed: Jun. 6, 1983

[51] Int. Cl.$^3$ .................. C07D 499/00; A61K 31/425
[52] U.S. Cl. ............................. 260/245.2 R; 424/270; 424/271
[58] Field of Search ................. 260/245.2 R, 245.2 T; 424/270

[56] References Cited

U.S. PATENT DOCUMENTS 4,180,506 12/1979 Pratt ................................. 260/245.2
4,420,426 12/1983 Moore ................................. 424/270
4,427,678 1/1984 Barth ............................ 260/245.2 R
4,432,970 2/1984 Kellogg ............................... 424/270

FOREIGN PATENT DOCUMENTS 13617 7/1980 European Pat. Off. .
2051046 1/1981 United Kingdom .

OTHER PUBLICATIONS

Clayton, J. Chem. Soc. (C) pp. 2123–2127 (1969).

*Primary Examiner*—Nicholas S. Rizzo
*Attorney, Agent, or Firm*—Charles J. Knuth; Albert E. Frost; Robert K. Blackwood

[57] ABSTRACT

A process for the debromination of 6-monobromo- and 6,6-dibromopenicillanic acid, and various derivatives thereof, by the action of a bisulfite salt. The debrominated compounds produced find various utilities, as beta-lactamase inhibitors useful in therapy in combination with known beta-lactam antibiotics, or as intermediates in the further synthesis of useful beta-lactam compounds.

15 Claims, No Drawings

PROCESS FOR DEBROMINATION OF DIBROMOPENICILLANIC ACID AND DERIVATIVES

BACKGROUND OF THE INVENTION

The present invention is directed to a process for the debromination of 6-monobromo- and 6,6-dibromopenicillanic acid, and various derivatives thereof, by the action of a bisulfite salt. The debrominated compounds produced by the present invention find various utilities, as beta lactamase inhibitors or as intermediates in the synthesis of further useful beta-lactam compounds, as noted below.

Similar debrominations have been previously carried by the means of trialkyl- or triaryltin hydrides. For example, European Patent Application No. 0,013,617 describes the conversion of benzyl 6-beta-bromopenicillanate to benzyl penicillanate by the action of tributyltin hydride and azobisisobutyronitrile in refluxing benzene; the conversion of various esters of 6,6-dibromopenicillanate to the corresponding 6-beta-bromopenicillanate with the same reagents; the conversion of benzyl 6,6-dibromopenicillanate 1,1-dioxide to a mixture of benzyl 6-alpha- and 6-beta-bromopenicillanates with the same reagent; and conversion of benzyl or pivaloyloxymethyl 6,6-dibromopenicillanates to a mixture of the corresponding 6-alpha- and 6-beta-bromo esters by use of triphenyltin hydride in place of tributyltinhydride.

That same European Patent Application further describes the use of methyllithium at -78° C., followed by acetic acid quench, for the low yield conversion of pivaloyloxymethyl 6,6-dibromopenicillanate to the corresponding 6-beta-bromo ester.

Pratt, U.S. Pat. No. 4,180,506, describes catalytic hydrogenation of 6,6-dibromopenicillanic acid over Pd/C catalyst to produce a mixture of 6-alpha- and 6-beta-bromopenicillanic acid. Clayton, J. Chem. Soc. (C), pp. 2123–2127 (1969), describes the hydrogenation of methyl 6,6-dibromopenicillanate over Pd/CaCO₃ to produce methyl 6-alpha-bromopenicillanate and methyl penicillanate; and hydrogenation of 6,6-dibromopenicillanic acid over the same catalyst to produce penicillanic acid.

U.K. Patent Application No. 2,051,046 describes the conversion of 6,6-dibromopenicillanic acid salts to 6-beta-bromopenicillanic acid, and pivaloyloxymethyl 6,6-dibromopenicillanate to pivaloyloxymethyl 6-beta-bromopenicillanate, with NaBH₄ or NaCNBH₃ as reagent.

SUMMARY OF THE INVENTION

The present invention is concerned with a process for the preparation of monobromo compound of the formula

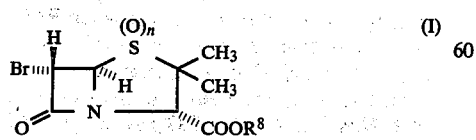

wherein n is 0, 1 or 2 and $R^8$ is hydrogen, a conventional carboxy protecting group removable by hydrogenolysis or a conventional ester forming radical which is hydrolyzable under physiological conditions, which comprises treatment of a dibromo compound of the formula

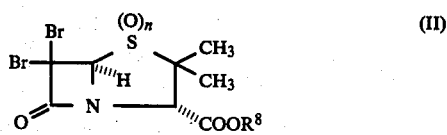

wherein n and $R^8$ are as previously defined, with one molar equivalent of a bisulfite salt in a reaction inert aqueous solvent at 0–100° C. The preferred temperature range, particularly when $R^8$ is a hydrolyzable ester, is 0–40° C. In that lower temperature range, an excess bisulfite can be used to increase reaction rate, without significant loss of the second bromine.

The process of the present invention is also useful in the preparation of a desbromo compound of the formula

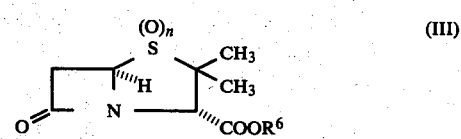

wherein n is as defined above and $R^6$ is hydrogen or a conventional carboxy protecting group removable by hydrogenolysis, which comprises treatment of a alpha- or beta-bromo compound of the formula

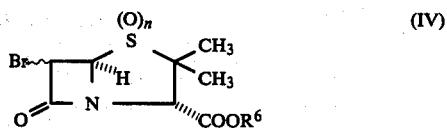

wherein n and $R^6$ are as defined above, with at least one molar equivalent of a bisulfite salt; or a dibromo compound of the formula

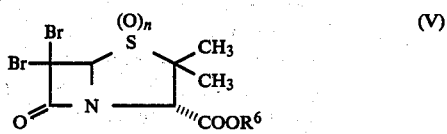

wherein n and $R^6$ are as defined above, with at least two molar equivalents of a bisulfite salt in a reaction inert aqueous solvent at 50–100° C.

The present process is also useful for the preparation of a mixture of 6-alpha and 6-beta compounds of the formula

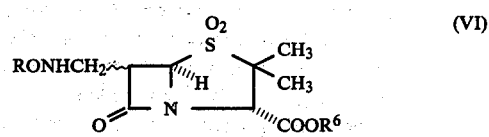

wherein R is ($C_1$–$C_4$) alkyl or benzyl and $R^6$ is hydrogen or a conventional carboxy protecting group removable by hydrogenolysis, which comprises treatment of a bromo compound of the formula

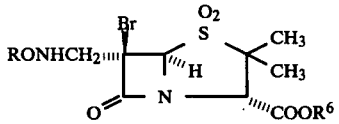

(VII)

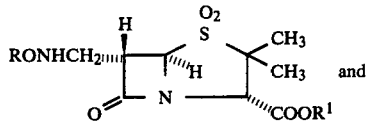

(VIII)

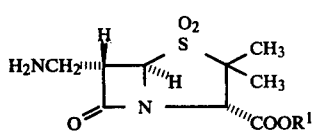

(IX)

wherein R and $R^6$ are as previously defined, with at least one molar equivalent of a bisulfite salt in a reaction inert aqueous solvent at 50–100° C.

The nature of the cation associated with the bisulfite anion is not a critical part of the present invention, although an alkali metal, particularly sodium, is generally preferred.

Except when $R^8$ is an ester radical which is hydrolyzable under physiological conditions, it is preferred to carry out the process of the present inventin in the presence of a mildly basic buffering substance. One to three molar equivalents of sodium bicarbonate are particularly well suited for this purpose.

The references to esters which are hydrolyzable under physiological conditions is directed to those esters frequently referred to as "pro-drugs". Such esters are now as well-known and common in the penicillin art as pharmaceutically acceptable salts. Such esters are generally used to enhance oral absorption, but in any event are readily hydrolyzed in vivo to the parent acid. The preferred ester forming radicals are:

gamma-butyrolacton-4-yl,

—$CHR^2OCOR^3$, and

—$CHR^2OCOOR^3$, wherein $R^2$ is hydrogen or methyl and $R^3$ is ($C_1$–$C_6$) alkyl. The most preferred radicals are pivaloyloxymethyl and 1-ethoxycarbonyloxyethyl.

Conventional carboxy protecting groups removable by hydrogenolysis are also very common in the penicillin art. In the present instance, benzyl, benzydryl and 2-naphthylmethyl are preferred examples of such groups, but the invention should not be so construed as limited to these three hydrogenolyzable groups.

As used herein the expression "reaction-inert solvent" defines a solvent which does not interact with starting materials, reagents, intermediates or products in a manner which significantly reduces the yield of the desired product. Well suited for the present process is water, preferably in combination with a relatively low boiling water miscible organic solvent such as tetrahydrofuran.

The compounds of the formula (III) wherein n is 2 and $R^6$ is hydrogen are beta-lactamase inhibitors, useful in therapy in combination with beta-lactam antibiotics (see Barth, U.S. Pat. No. 4,234,579). Otherwise the prime utility of the compounds of the formula (III) wherein n is other than 2 and/or $R^6$ is a hydrogenolyzable group is in the synthesis of those compounds of the formula (III) wherein n is 2 and/or $R^6$ is hydrogen, by oxidation of sulfur (n=0) or sulfoxide (n=1) with peracid and/or hydrogenolysis of the hydrogenolyzable ester group, according to methods well known in the penicillin art.

The prime utility of the compounds of the formulae (I) and (VI) is as intermediates in the synthesis of beta-lactamase inhibitors of the formulae wherein R is ($C_1$–$C_4$)alkyl or benzyl; and $R^1$ is hydrogen or a conventional ester forming radical which is hydrolyzable under physiological conditions; the pharmaceutically acceptable cationic salts thereof when $R^1$ is hydrogen; and pharmaceutically acceptable acid addition salts thereof.

Pharmaceutically acceptable cationic salts include, but are not limited to, those of sodium, potassium, calcium, N,N'-dibenzylethylenediamine, N-methylglucamine (meglumine) and diethanolamine. Pharmaceutically acceptable acid addition salts include, but are not limited to, those formed with HCl, $H_2SO_4$, $HNO_3$, $CH_3SO_2H$ and $pCH_3C_6H_4SO_3H$.

The compounds of the formula (IX) are an object of co-pending patent application Ser. No. 434,371, filed Oct. 21, 1982 for "6-Aminoalkylpenicillanic Acid 1,1-Dioxides as beta-Lactamase Inhibitors" by Barth. Processes for the ocmpounds (IX) which employ present intermediates are illustrated below and in concurrently filed patent application, Ser. No. 501,476 filed June 6, 1983 for "Process for 6-(Aminomethyl)-penicillanic Acid and Derivatives Thereof", also by Barth.

The compounds of the formula (VIII) and processes therefor employing presently produced intermediates are an object of concurrently filed patent application, Ser. No. 501,475 filed June 6, 1983 for "beta-Lactamase Inhibiting 6-(Alkoxyaminomethyl)penicillanic Acid 1,1-Dioxide and Derivatives" by Pirie, Volkmann and Kleinman. These various processes are also illustrated below.

DETAILED DESCRIPTION OF THE PRESENT INVENTION

The process of the present invention is readily carried out, according to the methods summarized above and detailed in specific examples below.

The starting materials required for the present process are either known compounds (many of which are described in references cited above, or they are prepared according to specific preparations as exemplified and detailed below.

As noted above, beta-lactamase inhibiting compounds of the formulae (VIII) and (IX) are conveniently synthesized from debrominated compounds prepared by the process of the present invention. For example, from compounds (I), when $R^8$ is in the acid (or salt) form, that group is converted to a hydrogenolyzable or hydrolyzable ester, in either case, using methods well known in the penicillin art (see for example, U.S. Pat. Nos. 4,234,579, 4,287,181 and 4,348,264). Furthermore, those compounds (I) wherein n is 1 or 0 are oxidized with at least one or two equivalents of a peracid (conveniently m-chloroperbenzoic acid) in a reaction-inert solvent such as ethyl acetate at 0–50° C. The resulting compoung of the formula (I) wherein $R^8$ is a hydrogenolyzable or hydrolyzable ester group and n is 2 is then converted, at −50 to −100° C. in an ethereal solvent (such as THF/ether) by the action of a simple Grignard reagent such as CH3dMgBr, into the 6-alpha Grignard reagent:

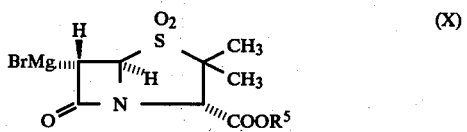

wherein $R^5$ is a hydrogenolyzable or hydrolyzable ester group as defined above for $R^8$.

Without isolation, the Grignard reagent (X) is reacted with formaldehyde O-alkyl- or O-benzyloxime in the presence of $BF_3$ to yield compounds of the formula

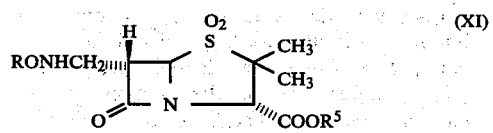

wherein R and $R^5$ are as defined above. When $R^5$ is a hydrolyzable ester, the compounds (XI) correspond to above compounds (VIII) wherein $R^1$ is the corresponding hydrolyzable ester. Those compounds (XI) wherein $R^5$ is a hydrolyzable ester may alternatively be hydrolyzed in mildly aqueous base to compounds of the formula (VIII) wherein $R^1$ is hydrogen. However, when R is other than benzyl, it is preferred to prepare compounds of the formula (VIII) wherein $R^1$ is hydrogen by the noble metal catalyzed hydrogenolysis of compounds of the formula (XI) wherein $R^5$ represents a hydrogenolyzable ester group.

Alternatively, the Grignard reagents (X) are reacted in situ with benzyl N-(acetoxymethyl)carbamate, in the presence of a second equivalent of $CH_3MgBr$, to yield a compound of the formula

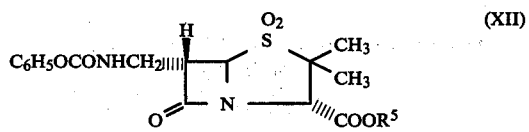

wherein $R^5$ is as defined above. When $R^5$ is a hydrogenolyzable group, noble metal catalyzed hydrogenolysis of the compounds (XII) yields the compounds (IX) wherein $R^1$ is hydrogen. When $R^5$ is hydrolyzable group (preferably resistant to hydrogenolysis), the compounds (IX) wherein $R^1$ is an in vivo hydrolyzable ester group are obtained.

The compounds (IX) are also obtained by Raney nickel catalyzed hydrogenation of the compounds (XI) or (VIII). When $R^1$ is hydrogen or $R^5$ is a hydrogenolyzable group in the substrate, $R^1$ is hydrogen in the product; when $R^5$ is hydrolyzable group (preferably without tendency to hydrogenolyze) $R^1$ is retained as the in vivo hydrolyzable group in the product.

The above mixed product (VI) obtained by the present process (before or after noble metal or Raney nickel catalyzed hydrogenolysis when $R^6$ is an ester) is readily converted to the single 6-alpha epimers (VIII) and (IX) wherein $R^1$ is hydrogen by the action of 1,5-diazabicyclo[4.3.0]non-5-ene.

Some of the compounds of the above formulae (VIII) and (IX), generally those wherein $R^1$ is hydrogen, have in vitro antibacterial activity. Such activity is demonstrated by measuring the minimum inhibitory concentrations (MIC's) in mcg/ml against a variety of microorganisms. The procedure which is followed is the one recommended by the International Collaborative Study on Antibiotic Sensitivity Testing (Ericcson and Sherris, Acta. Pathologica et Microbiologia Scandinasv, Supp. 217, Section B: 64–68 [1971]), and employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye.

Those compounds of the formulae (VIII) and (IX) having said in vitro antibacterial activity are thus useful as industrial antimicrobials, for example in water treatment, slime control, paint preservation and wood preservation, as well as for topical application as a disinfectant. In the case of use of these compounds for topical application, it is often convenient to admix the active ingredient with a non-toxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

The compounds of the formulae (VIII) and (IX) are of more particular value as potent inhibitors of microbial beta-lactamases. By this mechanism they increase the antibacterial effectiveness of beta-lactam antibiotic (penicillins and cephalosporins) against many microorganisms, particularly those which produce a beta-lactamase. The ability of these compounds to increase the effectiveness of a beta-lactam antibiotic can be appreciated by reference to experiments in which the MIC values of the antibiotic alone, and a compound of the formula (VIII) or (IX) (having $R^1$ as hydrogen) alone, are determined. These MIC's are then compared with the MIC values obtained with a combination of the given antibiotic and the compound of the formula (VIII) or (IX), wherein $R^1$ is hydrogen. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd Edition, 1974, American Society for Microbiology.

The compounds of the formulae (VIII) or (IX) enhance the antibacterial effectiveness of beta-lactam antibiotics in vivo. That is, they lower the amount of the antibiotic which is needed to protect mice against an otherwise lethal inoculum of certain beta-lactamase producing bacteria. In determining such activity, acute experimental infections are produced in mice by the intraperitoneal inoculation of the mice with a standardized culture of the test organism suspended in 5 percent hog gastric mucin. Infection severity is standardized so that the mice receive a lethal dose of the organism (the letal dose is the minimum inoculum of organism required to consistently kill 100 percent of the infected, non-treated control antibiotic is administered at various dosage levels, p.o. or i.p., to groups of infected mice. At the end of the test, the activity of the mixture is assessed by counting the number of survivors among treated animals at a given dose. Activity is expressed as the percentage of animals which survive at a given dose, or calculated as a $PD_{50}$ (dose which protects 50 % of the animals from infection).

The utility of compounds of the formula (VIII) and (IX) is alternatively assessed by a determination of blood levels following oral or parenteral dosage. Rats represent a convenient animal model for this purpose. When dosed as an in vivo hydrolyzable ester, the blood level is determined as the parent compound wherein $R^1$ is hydrogen. The blood level is determined by serial dilution bioassay technique using a microorganism such as *Pasturella multocida* which shows particular sensitivity to the parent compound.

The ability of the compounds of formulae (VIII) and (IX) to enhance the effectiveness of a beta-lactam antibiotic against beta-lactamase producing bacteria makes them valuable for co-administration with beta-lactam antibiotics in the treatment of bacterial infections in mammals, particularly man. In the treatment of a bacterial infection, the compound of the formula (VIII) or (IX) can be so-mingled with the beta-lactam antibiotic, and the two agents thereby administered simultaneously. Alternatively, the compound of the formula (VIII) or (IX) can be administered as a separate agent during a course of treatment with a beta-lactam antibiotic. In some instances it will be advantageous to predose the subject with the compound of the formula (VIII) or (IX) before initiating treatment with a beta-lactam antibiotic.

When using a compound of formula (VIII) or (IX) to enhance the effectiveness of beta-lactam antibiotic, a mixture of (VIII) or (IX) with the beta-lactam antibiotic is administered preferably in formulation with standard pharmaceutical carriers or diluents. A pharmaceutical composition a pharmaceutically acceptable carrier, a beta-lactam antibiotic and a compound of formula (VIII) or (IX) will normally contain from about 5 to about 80 percent of the pharmaceutically acceptable carrier by weight.

When using the compounds of formula (VIII) or (IX) in combination with another beta-lactam antibiotic, said compounds can be administered orally or parenterally, i.e., intramuscularly, subcutaneously or intraperitoneally. Although the prescribing physician will ultimately decide the dosage to be used in a human subject, the ratio of the daily dosages of the compounds of formula (VIII) or (IX) and the beta-lactam antibiotic will normally be in the range from about 1:3 to 3:1 by weight. Additionally, when using the compounds of formula (VIII) or (IX) in combination with another beta-lactam abtibiotic, the daily oral dosage of each component will normally be in the range from about 10 to about 200 mg per kilogram of body weight and the daily parenteral dosage of each component will normally be about 10 to about 40 mg per kilogram of body weight. These daily doses will usually be divided. In some instances, the prescribing physician will determine that dosages outside these limits are necessary.

As will be appreciated by one skilled in the art, some beta-lactam compounds are effective when administered orally or parenterally, while others are effective only when administered by the parenteral route. When a compound of formula (VIII) or (IX) is to be used simultaneously (i.e., co-mingled) with a beta-lactam antibiotic which is effective only on parenteral administeration, a combination formulation suitable for parenteral use will be required. When a compound of formula (VIII) or (IX) is to be used simultaneously (co-mingled) with a beta-lactam antibiotic which is effective orally or parenterally, combinations suitable for either oral or parenteral administration can be prepared. Additionally, it is possible to administer preparations of the compounds of formula (VIII) or (IX) orally, while at the same time administering a further beta-lactam antibiotic parenterally; and it is also possible to administer preparations of the compounds of formula (VIII) or (IX) parenterally, while at the same time administering the further beta-lactam antibiotic orally.

The present invention is illustrated by the following examples. However, it should be understood that the invention is not limited to the specific details of these examples. Unless otherwise specified, all operations were carried out at ambient temperatures; all temperatures are in °C., all drying of solutions was over anhydrous $Na_2SO_4$; all solvent evaporations were carried out in vacuo; and all pnmr (proton nuclear magnetic resonance) spectra were at 60 MHz. The abbreviations DMF, TEA, THF and DMSO are used, respectively, for N,N-dimethylformamide, triethylamine, tetrahydrofuran and dimethylsulfoxide. The abbreviation for milliliter appears variably as ml. or mL.

EXAMPLE 1

6-alpha-Bromopenicillanic Acid 1,1-Dioxide

To 6,6-dibromopenicillanic acid 1,1-dioxide (117.3 g, 0.3 mole), stirring in a mixture of $H_2O$ (600 mL) and ethyl acetate (400 mL), was added in portions $NaHCO_3$ (75.6 g, 0.9 mole) and then $NaHSO_3$ (37.5 g, 0.36 mole). After stirring 1 hour, the pH was adjusted from 3.7 to 1.5 with concentrated HCl. The aqueous layer was separated and extracted 1×400 mL with fresh ethyl acetate. The combined organic layers were backwashed with brine, dried and evaporated to yield title product as a solid; 72 g (76.7%); m.p. 136°–137°, pnmr/$D_2O$-$NaHCO_3$/delta: 1.48 (s, $CH_3$), 1.62 (s, $CH_3$), 4.28 (s, C.3—H), 5.12 (d, J=1.7, C.6—H), 5.37 (d, J=1.7, C.5—H).

EXAMPLE 2

Benzyl 6-alpha-Bromopenicillanate 1,1-Dioxide

To title product of the preceding Example (24.3 g, 0.0779 mole) in 75 mL DMF was added TEA (7.87 g, 0.0779 mole) and benzyl bromide (13.32 g, 0.0779 mole). The mixture was stirred 16 hours, poured into 250 mL $H_2O$ and extracted 2×200 mL ethyl acetate. The combined organic layers were washed with saturated $NaHCO_3$, $H_2O$ and brine, dried, evaporated to dryness and the residue crystallized from ethyl acetate/hexane; 28.8 g (92%); m.p. 72°–74°; pnmr/$CDCl_3$/delta (ppm): 1.27 (s, $CH_3$), 1.53 (s, $CH_3$), 4.53 (s, C.3H), 4.8 (d, J=1.7, C.6—H), 5.27 (d, J=1.7, C.5—H), 5.3 (d, $CH_2$), 7.5 (s, $C_6H_5$).

Substitution of benzyl bromide with benzhydryl chloride or 2-naphthylmethyl bromide produces the corresponding benzhydryl and 2-naphthylmethyl esters.

EXAMPLE 3

Ethyl 6-alpha-Bromopenicillanate

To a solution of ethyl 6,6-dibromopenicillanate (3.87 g, 0.01 mole) in THF (50 mL) was added $H_2O$ (50 mL), $NaHCO_3$ (1.68 g, 0.02 mole) and $NaHSO_3$ (1.04 g, 0.01 mole). The mixture was stirred 20 hours and the diluted with 100 mL ethyl acetate. The organic layer was separated, washed with $H_2O$ and then brine, dried and evaporated to yield title product as a solid, 2.5 g; pnmr/$CDCl_3$/TMS/delta (ppm) 1.30 (3H, t), 1.49 (3H, s), 1.62 (3H, s), 4.23 (2H, q), 4.51 (1H, s), 4.78 (1H, d $J=1.5Hz$), 5.38 (1H, da $J=1.5Hz$).

By the same procedure, benzyl 6,6-dibromopenicillanate 1,1-dioxide is converted to benzyl 6-alpha-bromopenicillanate 1,1-dioxide. The product initially obtained by that method is crystallized from ethyl acetate/hexane to yield product identical to that obtained according to Preparation 1 below.

By the same procedure, benzhydryl 6,6-dibromopenicillanate 1,1-dioxide is converted to benzhydryl 6-alpha-bromopenicillanate 1,1-dioxide; benzyl 6,6 dibromopenicillanate 1-oxide is converted to benzyl 6-alpha-bromopenicillanate 1-oxide; and naphthylmethyl 6,6-dibromopenicillanate is converted to naphthylmethyl 6-alpha-bromopenicillanate.

EXAMPLE 4

Penicillanic Acid 1,1-Dioxide

A mixture of 6,6-dibromopenicillanic acid 1,1-dioxide (3.92 g, 0.01 mole), $NaHCO_3$ (5.04 g, 0.06 mole) and $NaHSO_3$ (2.5 g, 0.024 mole) in 30 mL $H_2O$ was heated at 90° for 2 hours. The reaction mixture was cooled, acidified to pH 1.2 with dilute HCl and extracted with ethyl acetate. The extract was dried and evaporated to yield know title product, 180 mg; tlc Rf 0.1 compared to 0.4 for starting material (19:1 ethyl acetate:acetic acid); pnmr/$D_2O$ 1.45 (s, 3H), 1.58 (s, 3H), 3.47 (m, 2H), 4.22 (s, 1H), 4.97 (m, 1H).

By the same method, using one equivalent less of $NaHSO_3$ if desired, 6-alpha-bromopenicillanic acid 1,1-dioxide is converted to the same title product.

EXAMPLE 5

Mixture of Benzyl 6-alpha- and 6-beta-(Ethoxyaminomethyl)penicillanate 1,1-Dioxide Benzyl 6-beta-Bromo-6-1-alpha(ethoxyaminomethyl)-penicillanate 1,1-dioxide (1.0 g, 0.0021 mole), $NaHCO_3$ (177 mg, 0.0021 mole) and $NaHSO_3$ (220 mg, 0.0021 mole) were combined and stirred in 25 ml of 3:2 THF:$H_2O$ for 3 days, by which time tlc indicated reaction was about 50% complete. The reaction was then heated at 90° for 24 hours, stripped of THF and the aqueous solid containing residue extracted with $CHCl_3$. The extract was evaporated to a gum which was chromatographed on silica gel with $CHCl_3$ eluant to yield the title mixture in about 1:1 ratio; 270 mg; pnmr/$CDCl_3$ 1.08 (t, 3H), 1.28 (s, 3H), 1.53 (s, 3H), 3.42 (d, 2H), 3.78 (m, 3H), 4.55 (alpha—$C_3H$), 4.6 (beta—$C_3H$), 4.78 (m, alpha- and beta—$C_5H$), 5.32 (d, 2H), 7.52 (s, 5H); tlc Rf 0.42 (4:1 $CHCl_3$:ethyl acetate).

By the same procedure, mixtures of benzyl 6-alpha- and 6-beta-(methoxyaminomethyl)penicillanate 1,1-dioxides and benzyl 6-alpha- and 6-beta-(benzyloxyaminomethyl)penicillanate 1,1-dioxides are prepared.

EXAMPLE 6

Benzyl 6-alpha-(Ethoxyaminomethyl)-penicillanate 1,1-Dioxide

Title product mixture of the preceding Example (5.94 g, 0.015 mole) is stirred in 125 ml $CH_2Cl_2$, 1,5-diazabicyclo[4.3.0]nonene (1.86 g, 0.015 mole) is added, followed after 1 minute of stirring by $CH_3CO_2H$ (3.6 g, 0.06 mole) and after 2 more minutes of stirring, 100 mL of $H_2O$. The organic layer is separated, washed with 50 mL saturated $NaHCO_3$ and then 50 mL brine, dried and evaporated to yield title product.

By the same method, the other mixtures of the preceding Example are converted to benzyl 6-alpha-(methoxyaminomethyl)pencillanate 1,1-dioxide and benzyl 6-alpha-(benzyloxyaminomethyl)penicillanate 1,1-dioxide.

EXAMPLE 7

Pivaloyloxymethyl 6-alpha-Bromopenicillanate 1,1-Dioxide

Pivaloyloxymethyl 6,6-dibromopenicillanate 1,1-dioxide (505 mg, 1 mmole) and $NaHSO_3$ (208 mg) (2 mmole) were combined in 15 mL 2:1 THF:$H_2O$. After 1 hour, the THF was removed by evaporation and the aqueous residue extracted with $CH_2Cl_2$. The extract was dried and evaporated to yield title product, 300 mg; pnmr peaks identical to those of the product of Preparation 6 below, but showing contamination with starting material. Such contamination is avoided by extending the reaction time to about 4 to 6 hours.

The following Examples illustrate the use of the present compounds as intermediates in the synthesis of compounds of the formula (VIII) and (IX).

EXAMPLE 8

Benzyl 6-alpha-(Benzyloxycarbonylamino-methyl) penicillanate 1,1-Dioxide

Benzyl 6-alpha-bromopenicillanate 1,1-dioxide (0.804 g., 2.0 mmoles) in 30 ml. dry THF was cooled to −78°. Ethereal $CH_3MgBr$ (2.8M, 1.43 ml., 4.0 mmoles) was added over 3 minutes and stirring continued for 7 minutes at −78°, forming the corresponding 6-alpha-bromomagnesium Grignard reagent. A solution of benzyl N-(acetoxymethyl) carbamate (0.57 g., 2.0 mmole) in 5 ml. dry THF was then added. After stirring 5 minutes at −78°, the reaction mixture was quenched by the addition of 0.5 ml. $CH_3CO_2H$, the solvent evaporated and the residue taken up in $CHCl_3$, washed with $H_2O$, saturated $NaHCO_3$ and brine, dried and evaporated to a viscous oil (1.1 g.). The oil was chromatographed on 40 g. silica gel eluting with 1:19 ethyl acetate: chloroform in 20 ml. fractions. Fractions 5–8 were combined, evaporated to an oil (0.55 g.) which was crystallized by scratching in 10 ml. ether; 0.32 g.; pnmr/$CDCl_3$/delta/TMS 1.20 (3H, s), 1.49 (3H, s), 3.65 (3H, m), 4.32 (1H, s), 4.59 (1H, m), 5.07 (2H, s), 5.14 (2H, q), 5.30 (1H, br), 7.32 (1OH, s).

By the same procedure, benzhydryl 6-alpha-bromopenicillanic acid 1,1-dioxide is converted to benzhydryl 6-alpha-benzyloxycarbonylaminomethyl)-penicillanate 1,1-dioxide.

EXAMPLE 9

6-alpha-(Aminomethyl)penicillanic Acid 1,1-Dioxide

Title product of preceding Example (1.7 g.), THF (35 ml.), H$_2$O (35 ml.) and 10% Pd/C (1.7 g.) were combined and hydrogenated at 50 psig for 1 hour. Catalyst was recovered by filtration and THF removed from the filtrate in vacuo. The aqueous layer was washed with 30 ml. ethyl actate, and the aqueous layer concentrated to yield crystalline title product; 0.7 g.; pnmr/250 MHz/D$_2$O/DSS 1.44 (H, s), 1.59 (3H, s), 3.63 (2H, d, J=5.5Hz), 4.07 (1H, td, J=2, 5.5Hz), 4.31 (1H, s), 5.06 (1H, d, J=2).

The same product is obtained by hydrogenolysis of the benzydryl ester of the preceding Example.

EXAMPLE 10

R- and S-1-(Ethoxycarbonyloxy)ethyl 6-alpha-Bromopenicillanate 1,1-Dioxide 6-alpha-Bromopenicillanic acid (31 g.) was dissolved in 500 ml. CH$_2$Cl$_2$ and diluted with 200 ml. H$_2$O. NaHCO$_3$ (9.3 g.) was added, followed by the portionwise addition of tetrabutylammonium bisulfate (37.6 g.) while maintaining pH 7.5–8.0 with 2N NaOH. The organic layer was separated, washed with brine, dried and evaporated to yield tetrabutylammonium 6-alpha-bromopenicillanate as an oil (57.8 g.).

The oil and alpha-chlorodiethyl carbonate (25.3 ml.) were dissolved in 500 ml. acetone and stirred in the dark under N$_2$ for 36 hours. The reaction mixture was evaporated to a second oil and chromatographed on 1 Kg. silica gel, eluting with 1:4 hexane:CHCl$_3$ and collecting 20 ml. fractions. Fractions 33-100 were combined and evaporated to yield crude 1-(ethoxycarbonyloxy)ethyl 6-alpha-bromopenicillante as a third oil (41 g.).

The latter and m-chloroperbenzoic acid (30 g.) were taken into 500 ml. ethyl acetate, stirred under N$_2$ for 20 hours, washed in sequence with 3×50 ml., saturated NaHSO$_3$, 3×100 ml. saturated NaHCO$_3$ and 1×100 ml. brine, dried and evaporated. The resulting residue was chromatographed in 1 Kg. fresh silica gel, developed with 3 l. of 1:1 hexane:CHCl$_3$ and then eluted with CHCl$_3$ in 25 ml. fractions.

Less polar 81-160 were combined and evaporated to a white foam (15.8 g.) which crystallized on combining with 50 ml. ether and scratching to yield the title procuct of S-stereochemistry; 5.2 g.; m.p. 140–143°; tlc (1.99 ethyl acetate:CHCl$_3$) Rf 0.65; pnmr/CDCl$_3$/TMS/delta (ppm): 1.27 (3H, t, J=7Hz), 1.46 (3H, s), 1.55 (3H, s), 1.58 (3H, d, J=5.5Hz), 4.20 (2H, q, J=7Hz), 4.35 (1H, s), 4.65 (1H, d, J=2Hz), 5.09 (1H, d, J=2Hz), 6.67 (1H, q, J=5.5).

Anal. Calcd. for C$_{13}$H$_{18}$O$_8$NSBr: C, 36.45; H, 4.23; N, 3.27. Found: C, 36.47; H, 4.30; N, 3.31.

More polar fractions 161-200 were combined and evaporated to a second while foam (4.1 g.) which also crystallized on combining with 50 ml. ether and scratching to yield the title product of R-stereochemistry; 2.8 g.; m.p. 114°–114.5°; tlc (1:9 ethyl acetate:CHCl$_3$) Rf 0.55; pnmr/CDCl$_3$/TMS/delta (ppm): 1.32 (3H, t, J=7Hz), 1.45 (3H, s), 1.59 (3H, d, J=5.5), 1.62 (3H, s), 4.21 (2H, q, J=7Hz), 4.41 (1H, s), 4.63 (1H, d, J=2Hz), 5.11 (1H, d, J=2Hz), 6.77 (1H, q, J=5.5).

Anal. Calcd. for C$_{13}$H$_{18}$O$_8$NSBr: C, 36.45; N, 4.23; N, 3.27. Found: C, 36.48; H, 4.26; N, 3.28.

EXAMPLE 11

S-1-(Ethoxycarbonyloxy)ethyl 6-alpha-(Benzyloxycarbonylaminomethyl)penicillanate 1,1-Dioxide S-1-(Ethoxycarbonyloxy)ethyl 6-alpha-bromopenicillanate 1,1-dioxide (16.8 g., 0.0392 mole) was dissolved in 150 ml. dry THF and cooled to −78° C. Ethereal CH$_3$MgBr (2.9M, 24.3 ml., 0.0706 mole) was added over 5 minutes (to form the intermediate Grignard reagent), followed by a solution of benzyl N-(acetoxymethyl)carbamate (8.75 g., 0.0392 mole) in 20 ml. dry THF. After stirring at −78° C. for 30 minutes the reaction mixture was quenched with 8.5 ml. CH$_3$CO$_2$H, evaporated and the residue chromatographed on 600 g. silica gel, eluting with 1:19 ethyl acetate: CHCl$_3$, discarding the first 800 ml., then collecting 25 ml. fractions. Fractions 54–113 gave title product (9.9 g.). Center cuts 71–95 gave product of highest purity; 4.4 g.; pnmr/CDCl$_3$/TMS/delta (ppm): 1.30 (3H, t, J=7Hz), 1.40 (3H, s), 1.52 (3H, s), 1.56 (3H, d, J=5.5), 3.71 (3H, br. m), 4.22 (2H, q, J=7Hz), 4.32 (1H, s), 4.65 (1H, br. s), 5.10 (2H, s), 5.39 (1H, t, NH), 6.75 (1H, q, J=5.5), 7.33 (5H, s).

EXAMPLE 12

S-1-(Ethoxycarbonyloxy)ethyl 6-alpha-(Aminomethyl) penicillanate 1,1-Dioxide Hydrochloride Pd/C (10%, 3 g.) slurried in 30 ml. H$_2$O was hydrogenated at 4 atmospheres for 15 minutes. The pH dropped from 9.2 to 4.5. Title product of the preceding Example (3.3 g.) in 50 ml. THF was added and hydrogenation at 4 atmospheres continued for 15 minutes. Pd/C (10%, 2 g.) was added and hydrogenation continued for an additional 15 minutes. The catalyst was recovered by filtration over diatomaceous earth with 30 ml. H$_2$O/70 ml. THF for wash. THF for wash. THF was evaporated from the combined filtrate and wash. The aqueous residue was combined with 75 ml. ethyl acetate, the pH adjusted from 6.2 to 8.0 with 0.5N NaOH, and the organic layer separated. The organic layer was combined with 50 ml. fresh H$_2$O, adjusted to pH 4.0 with 0.5N HCl and the aqueous layer separated and freeze dried to yield title product; 1.05 g.; pnmr/D$_2$O/DSS/delta (ppm): 1.28 (3H, t, J=7Hz), 1.48 (3H, s), 1.58 (3H, d, J=5.5Hz), 1.60 (3H, s), 3.65 (2H, m), 4.07 (1H, m), 4.26 (2H, q, J=7Hz), 4.78 (1H, s), 5.13 (1H, d J=2Hz), 6.80 (1H, q, J=5.5).

EXAMPLE 13

R-1-(Ethoxycarbonyloxy)ethyl 6-alpha-(Benzyloxycarbonylaminomethyl)penicillante 1,1-Dioxide R-1-(Ethoxycarbonyloxy)ethyl 6-alpha-bromopenicillanate 1,1-dioxide (10.2 g., 0.0238 mole) was reacted and product isolated according to Example 11. The crude product was chromatographed on 700 g. silica gel, developed with 1000 ml. 1:19 ethyl acetate:CHCl$_3$ and then eluted with 1:9 ethyl acetate:CHCl$_3$, collecting 25 ml. fractions. Fractions 101-136 gave title product (6.8 g.). Center cuts 111-136 gave highest purity title product; 3.8 g.; pnmr/CDCl$_3$/TMS/delta (ppm): 1.30 (3H, t, J=7Hz), 1.38 (3H, s), 1.54 (3H, d, J=5.5Hz), 1.56 (3H, s), 3.71 (3H, br. m), 4.21 (2H, q, J=7Hz), 4.37 (1H, s), 4.64 (1H, br. s), 5.09 (2H, s), 5.45 (1H, t, NH), 6.77 (1H, q, J=5.5Hz), 7.30 (5H, s).

EXAMPLE 14

R-1-(Ethoxycarbonyloxy)ethyl 6-alpha-(Aminomethyl)penicillanate 1,1-Dioxide Hydrochloride By the procedure of Example 4, title product of the preceding Example (3.8 g.) was converted to present title product; 0.8 g.; pnmr/$D_2O$/DSS/delta (ppm): 1.27 (3H, t, J=7Hz), 1.45 (3H, s), 1.58 (3H, d, J=5.5Hz), 1.61 (3H, s), 3.64 (2H, m), 4.04 (1H, m), 4.13 (2H, q, J=7Hz), 4.76 (1H, s), 5.12 (1H, d, J=2Hz), 6.78 (1H, q, J=5.5).

EXAMPLE 15

Benzyl 6-alpha-(Methoxyaminomethyl)- penicillanate 1,1-Dioxide

Benzyl 6-alpha-Bromopenicillanate 1,1-Dioxide (4.02 g, 0.01 mole) in dry THF (75 mL) was stirred at −75° under $N_2$. Methylmagnesium bromide (2.98M in ether; 3.35 mL, 0.01 mole) was added dropwise over 3 minutes maintaining less than −67°. Formaldehyde O-methyloxime (0.59 g, 0.01 mole) in THF (25 mL) was cooled to −70°, and $BF_3$ etherate (1.42 g, 0.01 mole) added. The resulting solution of complex was added to the above Grignard solution at −70° and the mixture stirred 1 hour at −70 to −76°. Acetic acid (2 mL) was added over 3 minutes and the reaction mixture warmed and evaporated. The residue was distributed in 50 mL $H_2O$ and 100 mL ethyl acetate. The aqueous layer was at pH 1.7. The ethyl acetate layer was separated, washed with saturated $NaHCO_3$ (75 mL) and then brine, dried and evaporated to a gum (3.58 g). Chromatography on silica gel, eluting with 4:1 $CHCl_3$:ethyl acetate gave purified title product as a gum; 1.88 g; tlc $R_f$ 0.3 (3:1 $CHCl_3$:ethyl acetate); pnmr/$CDCl_3$/delta ( m) 1.3 (s, $CH_3$), 1.57 (s, $CH_3$), 3.47 (m, $NCH_2$), 3.58 (s, $OCH_3$), 4.0 (m, C.6—H), 4.52 (s, C. 3—H), 4.82 (d, J=1.7, C.5—H), 5.33 (d, $OCH_2$), 7.57 (s, $C_6H_5$).

EXAMPLE 16

6-alpha-(Methoxyaminomethyl)penicillanic Acid 1,1-Dioxide

Title product of the preceding Example (4.7 g, 0.0123 mole) in 150 mL 10:1 THF:$H_2O$ was hydrogenated over 3.5 g 10% Pd/C (50% water wet) under 4 atmospheres pressure of $H_2$ for 2 hours, monitoring by tlc. Catalyst was removed by filtration, and the filtrate was evaporated to yield present title product as a tacky solid; tlc $R_f$ 0.70 (6:1:1 acetone:$CH_3CO_2H$:$H_2O$). The entire batch was used in the next Example.

By the same method title product of Example 19 below is converted to 6-alpha-(ethoxyaminomethyl)-penicillanic acid 1,1-dioxide.

EXAMPLE 17

Sodium 6-alpha-(Methoxyaminomethyl)penicillanate 1,1-Dioxide

By dissolving in 10:1 $H_2O$:acetone, adjusting the pH to 7 with one equivalent $NaHCO_3$ and freeze drying the entire batch of title product from the preceding Example was converted to present title product; 3.2 g; pnmr/$D_2O$/delta (ppm): 1.43 (s, $CH_3$), 1.57 (s, $CH_3$), 3.42 (m, $CH_2$), 3.53 (s, $OCH_3$), 3.86 (m, C.6—H), 4.2 (s, C.3—H); 4.95 (d, J=1.7, C.5—H); ir (KBr) 1777, 1621 $cm^{-1}$.

EXAMPLE 18

6-alpha-(Aminomethyl)penicillanic Acid 1,1-Dioxide

Title product of Example 15 (0.5 g, 0.0013 mole) in 3:1 THF:$H_2O$ (20 mL) was hydrogenated over 500 mg of Raney nickel catalyst under 4 atmospheres of hydrogen for 2 hours, monitoring by tlc. The reaction was filtered and filtrate evaporated to yield title product as a white solid identical in all respects with authentic material; pnmr/$D_2O$/delta (ppm): 1.42 (s, $CH_3$), 1.57 (s, $CH_3$), 3.55 (m, $CH_2$), 3.97 (m, C.6—H), 4.22 (s, C.3—H), 4.98 (d, J=1.7, C.5—H); tlc $R_f$ 0.3 (6:1:1 acetone:$CH_3CO_2H$:$H_2O$).

By the same method, title product of Example 24 (0.28 g) was converted to the same title product, which was further purified by dissolving in $H_2O$, washing with ethyl acetate, treatment with activated carbon, and evaporation with THF chase; 0.08 g.

EXAMPLE 19

Benzyl 6-alpha-(Ethoxyaminomethyl)penicillanate 1,1-Dioxide

Title product of Example 2 (80.6 g, 0.20 mole) in 800 mL dry THF was cooled to −70°. $CH_3MgBr$ (69 mL of 2.9M in ether, 0.20 mole) was added over 40 minutes, maintaining temperature by the rate of addition. Meanwhile, in a separate flask formaldehyde O-ethyloxime (16.3 g, 0.22 mole) and $BF_3$.etherate (31.2 g, 26.9 mL, 0.22 mole) in 100 mL dry THF was cooled to −70°. As soon as $CH_3MgBr$ addition was complete, the latter solution was added all at once to the former solution. The temperature, which rose to −60°, was reduced to −70° and the mixture stirred 1 hour. $CH_3CO_2H$ (28.6 mL, 0.5 mole) was added over 15 minutes, maintaining less than 31 60°. The mixture was evaporated to a foam which was distributed between 700 mL $CH_2Cl_2$ and 400 mL $H_2O$ and the pH adjusted to 8 with saturated $NaHCO_3$. The resulting emulsion was broken by the addition of ethyl acetate. The organic layer was separated, washed with brine, dried and evaporated to an oil. The oil was chromatographed on a short silica gel column, first eluting less polar impurities with $CHCl_3$ and then eluting crude product with ethyl acetate. The latter was isolated as a second oil, which was rechromatographed on 500 g silica gel eluted with 1:19 ethyl acetate:$CHCl_3$, monitored by tlc. Pure product fractions were combined and evaporated to yield purified title product as an oil, 13.9 g, tlc $R_f$0.4 (4:1 $ChCl_3$:ethyl acetate).

EXAMPLE 20

6-alpha-(Aminomethyl)penicillanic Acid 1,1-Dioxide

By the method of Example 18, title product of the preceding Example (13.9 g) was hydrogenated over Raney nickel. After removing the catalyst by filtraion, THF was removed by evaporation and impurities extracted away with ethyl acetate, forming a clean, aqueous solution of title product used directly in the next Example; tlc $R_f$ 0.3 (6:1:1 acetone:$CH_3CO_2H$:$H_2O$). Alternatively, title product is isolated by further evaporation or freeze drying to yield product identical to that of Example 9.

EXAMPLE 21

6-alpha-(Benzyloxycarbonylaminomethyl)penicillanic Acid 1,1-Dioxide

Method A

The entire aqueous solution of title product of the preceding Example was diluted with 150 mL THF and stirred at 5°. The pH was adjusted to 8 with 25% NaOH and maintained at 8–8.5 during the 10 minute reaction which followed the addition of benzyl chloroformate (6.05 g, 0.35 mole). THF was removed by evaporation and the aqueous residue extracted with ether. The aqueous layer was covered with ethyl acetate and adjusted to pH 1.5 with 6N HCl. The aqueous layer was extracted with fresh ethyl acetate. The ethyl acetate layers were combined, dried and evaporated to yield title product; 7.08 g (50.7% over 2 steps); pnmr/CDCl$_3$/TMS 1.40 (3H, s), 1.55 (3H, s), 3.70 (3H, m), 4.31 (1H, s), 4.58 (1H, m), 5.04 (2H, s), 7.24 (5H, s).

Method B

Title product of Example 9 or 18 (3.0 g, 11.45 mmoles) was dissolved in 100 mL 1:1 H$_2$O:methanol. The pH was adjusted and maintained at 8.3–8.7 as benzyl chloroformate (1.79 g, 12.59 mmoles) was added dropwise over several minutes. Following a brief period of stirring the pH was adjusted to 6.0 with 1N HCl and THF removed by distillation in vacuo. The aqueous residue was extracted with 30 mL of ethyl acetate and the extract discarded. Fresh ethyl acetate (50 mL) was added and the pH adjusted to 1.8 with 1N HCl. The aqueous layer was extracted with 50 mL fresh ethyl acetate. The combined organic layer and extract was washed 1×50 mL saturated NaCl, dried (Na$_2$SO$_4$) and evaporated in vacuo to yield title product as a foam, 3.7 g, having pnmr identical with that of title product obtained according to Method A immediately above.

EXAMPLE 22

Pivaloyloxymethyl 6-alpha-(Benzyloxycarbonylaminomethyl)penicillanate 1,1-Dioxide

Method A

The title product of the preceding Example 6.75 g, 17 mmoles) and N,N-diisopropylethylamine (3.34 mL, 18.7 mmoles) were dissolved in dimethylformamide (50 ml), chloromethyl pivalate (2.72 mL, 18.7 mmoles) added, and the mixture allowed to stir at ambient temperature for 20 hours. The reaction mixture was diluted with ethyl ether (300 mL), washed with water (2×100 mL), dried (Na$_2$SO$_4$) and evaporated in vacuo to an oil. The oil was dissolved in 100 mL ether, washed 3×50 mL H$_2$O, dried (Na$_2$SO$_4$) and concentrated in vacuo to yield purified title product as a viscous oil, 4.4 g, pnmr/CDCl$_3$/TMS 1.20 (9H, s), 1.34 (3H, s), 1.51 (3H, s), 3.64 (3H, m), 4.31 (1H, s), 4.60 (1H, d), 5.04 (2H, s), 5.71 (2H, q), 7.24 (5H, s).

Method B

By the method of Examples 8, 11 and 13, pivaloyloxymethyl 6-alpha-bromopenicillanate 1,1-dioxide is converted to the corresponding Grignard reagent in situ and then reacted with an equivalent of benzyl N-(acetoxymethyl)carbamate, in the presence of a second equivalent of CH$_3$MgBr, to yield the present title product.

EXAMPLE 23 p-Toluenesulfonate Salt of Pivaloyloxymethyl 6-alpha-(Aminomethyl)penicillanate 1,1-Dioxide

Method A

Title product of the preceding Example (1.8 g, 3.53 mmoles) was hydrogenated in a mixture of THF (40 mL) and H$_2$O (20 mL) over 1.8 g of 10% Pd/C in the presence of pyridinium p-toluenesulfonate (1.77 g, 7.06 mmoles) at 4atmospheres for 1.5 hours. The catalyst was recovered by filtration over diatomaceous earth and the filtrate stripped of THF in vacuo, during which the title product crystallized, 1.2 g, mp 214°-215° C. (dec.); pnmr/DMSO-d$_6$/TMS 1.16 (9H, s), 1.32 (3H, s), 1.48 (3H, s), 2.28 (3H, s), 3.34 (2H, m), 3.82 (1H, m), 4.60 (1H, s), 5.14 (1H, d, J=2 Hz), 5.75 (2H, ABq), 7.23 (4H, ABq).

Anal. Calcd. for C$_{15}$H$_{24}$O$_7$N$_2$S.C$_7$H$_7$SO$_3$H: C, 48.16; H, 5.88; N, 5.11. Found: C, 48.31; H, 6.11; N, 5.08.

Method B

Title product of the preceding Example (5.28 g, 10.35 moles) in 70 mL THF was added to a slurry of 10% Pd/C (2.5 g) which had been prehydrogenated in 70 mL H$_2$O. The mixture was hydrogenated for 30 minutes at 50 psig. After recovery of the catalyst, p-toluenesulfonic acid (2.16 g) in 5 mL of H$_2$O was added to the filtrate and the identical title product recovered by filtration. 4.08 g (71.9%).

EXAMPLE 24

Benzyl 6-alpha-(Benzyloxyaminomethyl)penicillanate 1,1-Dioxide

According to the procedure of Example 15, using a reaction time of 1 hour at −70° following addition of BF$_3$/formaldehyde O-benzyloxime, benzyl 6-alpha-bromopenicillanate 1,1-dioxide (5.8 g, 0.014 mole) was converted to present title product. Following initial stripping of the quenched reaction mixture, the residual oil was dissolved in 100 mL ethyl acetate, washed 2×50 mL saturated NaHCO$_3$ and 1×50 mL brine, dried and restripped to a second oil, solidified by trituration with CCl$_4$ and ether to yield crude title product, 2.16 g. The latter was chromatographed on 90 g silica gel eluting with 2:1 cyclohexane:ethyl acetate to yield purified title product, 0.3 g; tlc Rf 0.5 (3:1 CHCl$_3$:ethyl acetate); pnmr/CDCl$_3$/TMS/delta (ppm) 1.27 (s, 3H), 1.53 (s, 3H), 3.33 (m, 2H), 3.93 (m, 1H), 4.5 (s, 1H), 4.75 (s, 2H), 5.27 (s, 2H), 7.45 (s, 5H), 7.48 (s, 5H).

EXAMPLE 25

Pivaloyloxymethyl 6-alpha-(Ethoxyaminomethyl)penicillanate 1,1-Dioxide

Pivaloyloxymethyl 6-alpha-bromopenicillanate 1,1-dioxide (5.0 g, 0.0118 mole) in 160 mL THF was cooled to −100° in a liquid N$_2$/ether bath. At the same time, formaldehyde O-ethyloxime (1.1 g, 0.0147 mole) in 100 mL THF was cooled to −75° in separate flask. CH$_3$MgBr (6.45 mL of 2.28M in ether, 0.0147 mole) was added over 2 minutes to the first solution, as BF$_3$. Etherate (1.8 mL, 2.1 g, 0.0147 mole) was added to the second. The second solution was immediately added to the first solution in one portion; the temperature rose to −80°. The reaction mixture was stirred 10 minutes at −90°, 20 minutes at −75° and 40 minutes at −65°, quenched by the addition of 1.6 mL CH$_3$CO$_2$H at the latter temperature, warmed and evaporated to an oil which was chased with ethyl acetate. The oil was partitioned between 100 mL ethyl acetate and 50 mL H$_2$O. The organic layer was separated, washed 2×50 mL H$_2$O and 1×50 mL and evaporated to a 4.8 g residue. The latter was chromatographed on silica gel, eluting with 2:1 hexane:ethyl acetate in 50 mL fractions. Fractions 21-31 were combined and evaporated to yield title product; 0.82 g; pnmr/CDCl$_3$/TMS/delta (ppm) 1.17 (t, 3H), 1.23 (s, 9H), 1.45 (s, 3H), 1.62 (s, 3H), 3.48 (m,2 H), 3.87 (q, 2H), 4.1 (m, 1H), 4.51 (s, 1H), 4.83 (d, 1H, J=1.8 Hz), 5.98 (q, 2H).

EXAMPLE 26 p-Toluenesulfonte Salt of Pivaloyloxymethyl 6-alpha-(Aminomethyl)penicillanate 1,1-Dioxide Title product of the preceding Example (0.6 g) was hydrogenated over Raney nickel according to the procedure of Example 18 and present title product isolated according to Example 23, Method B. Yield: 360 mg, identical to the product of Example 23.

PREPARATION 1

Benzyl 6-alpha-Bromopenicillanate 1,1-Dioxide

To title product of Example 1 (24.3 g, 0.0779 mole) in 75 mL DMF was added TEA (7.87 g, 0.0779 mole) and benzyl bromide (13.32 g, 0.0779 mole). The mixture was stirred 16 hours, poured into 250 mL H$_2$O and extracted 2×200 mL ethyl acetate. Th combined organic layers were washed with saturated NaHCO$_3$, H$_2$O and brine, dried, evaporated to dryness and the residue crystalized from ethyl acetate/hexane; 28.8 g (92%); m.p. 72°-74°; pnmr/CDCl$_3$/delta (ppm): 1.27 (s, CH$_3$), 1.53 (s, CH$_3$), 4.53 (s, C.3H), 4.8 (d, J=1.7, C.6—H), 5.27 (d, J=1.7, 1 C.5—H), 5.3 (d, CH$_2$), 7.5 (s, C$_6$H$_5$).

PREPARATION 2

Benzyl 6,6-Dibromopenicillanate 1,1-Dioxide

By the method of the preceding Preparation, 6,6-dibromopenicillanic acid 1,1-dioxide (39.2 g) was converted to present title product; 37 g (77%); m.p. (crude) 134°-136°, (recrystallized) 146°-148°; pnmr/CDCl$_3$/delta (ppm): 1.27 (s, CH$_3$), 1.55 (s, CH$_3$), 4.62 (s, C.3-H), 5.13 (S, C.5—H), 5.3 (d, CH$_2$), 7.46 (s, C$_6$H$_5$).

PREPARATION 3

Benzyl 6-beta-Bromo-6-alpha-(Methoxyaminomethyl)penicillanate 1,1-Dioxide

By the method of Example 15, title product of the preceding Preparation (26.17 g, 0.0544 mole) was converted to present title product (27.7 g of crude), purified by silica gel chromatography using 17:3 CHCl$_3$:ethyl acetate as eluant; 10.7 g (42.5%); m.p. 107°-109°; tlc R$_f$ 0.52 (17:3 CHCl$_3$:ethyl acetate); pnmr (250 MHz)/CDCl$_3$/delta (ppm): 1.28 (s, CH$_3$), 1.59 (s, CH$_3$), 3.54 (s, OCH$_3$), 3.6 (octet, NCH$_2$), 4.54 (s, C.3—H), 4.95 (s, C.5—H), 5.26 (q, OCH$_2$), 5.99 (q, NH), 7.39 (s, C$_6$H$_5$).

PREPARATION 4

Benzyl 6-beta-Bromo-6-alpha-(Ethoxyaminomethyl)penicillanate 1,1-Dioxide

Method A

Title product of Preparation 2 (27.5 g, 0.057 mole) in 900 mL dry THF was cooled to −75°. CH$_3$MgBr (19 mL of 2.9M in ether, 0.057 mole was added dropwise over 11 minutes, maintaining less than −70°. To this was added a solution of formaldehyde O-ethyloxime (4.2 g, 0.057 mole) and BF$_3$. etherate (8.1 g, 0.057 mole) in 125 mL THF precooled to −75°. After stirring 1 hour at −75°, CH$_3$CO$_2$H (11 mL) was added dropwise and the mixture evaporated and THF chased with ethyl acetate. The residue was distributed between 500 mL each H$_2$O and ethyl acetate and the pH adjusted from 2.8 to 1.5 with 6N HCl. The organic layer was washed with 50 mL fresh H$_2$O. The combined aqueous layers were back-washed with 25 mL ethyl acetate. The combined organic layers were washed 1×50 mL saturated NaHCO$_3$, 1×50 mL H$_2$O and 1×50 mL brine, dried, decolorized with activated carbon, evaporated (25.4 g) and chromatographed on silica gel eluting with 1:19 ethyl acetate:CHCl$_3$ and monitoring by tlc. Clean product fractions were combined and evaporated to yield title product; 9.7 g (35.9%); pnmr/CDCl$_3$/TMS 1.1 (t, 3H), 1.27 (s, 3H), 1.55 (s, 3H), 3.62 (m, 2H), 3.85 (q, 2H), 4.62 (s, 1H), 5.08 (s, 1H), 5.32 (d, 2H), 7.52 (s, 5H).

Method B

Title product of Preparation 2 (60 g, 0.125 mole) in 400 mL dry THF was cooled to −91°. CH$_3$MgCl (68.5 mL of 2M in ether, 0.136 mole) was added over 5 minutes, maintaining less than −85° with external liquid N$_2$ cooling. After stirring at −70° or lower for 45 minutes, formaldehyde O-ethyloxime (10.02 g, 0.137 mole) and then immediately BF$_3$.etherate (19.5 g, 0.137 mole) and then immediately BF$_3$.etherate (19.5 g, 0.137 mole) were added. After stirring at −70° for 1 hour the reaction was quenched with 24 mL CH$_3$CO$_2$H, then diluted with ethyl acetate (650 mL), warmed, washed 3×400 mL H$_2$O and evaporated to 150 mL. The resulting crystallized title product was recovered by filtration; 23.1 g; m.p. 130°-135°; pnmr as above Method A; an X-ray crystal structure analysis confirmed the structure of this product.

PREPARATION 5

Benzyl 6-beta-Bromo-6-alpha-(Benzyloxyaminomethyl)penicillanate 1,1-Dioxide

Title product of Preparation 2 (9.6 g, 0.02 mole) was reacted with methyl magnesium bromide (6.7 mL of 2.98M, 0.02 mole) at −50° to −α° over 15 minutes, and then with BF$_3$. etherate (2.5 mL, 0.02 mole)/formaldehyde O-benzyloxime (2.7 g, 0.02 mole) at −50° according to the method of Example 16. After 30 minutes at −60° and warming to −20° over 20 minutes, the mixture was quenched with 1 mL CH$_3$CO$_2$H and stripped of solvent. The residue was taken up in 100 mL each of saturated NaHCO$_3$ and ethyl acetate and the resulting emulsion broken with NaCl, and the aqueous layer extracted 2× fresh ethyl acetate. The organic layers were combined, back-washed 2× saturated NaHCO$_3$ and then brine, dried, stripped, and the residue chromatographed on 300 g silica gel with 1:5 ethyl acetate:-hexane as eluant and tlc monitoring. Clean product fractions were combined and evaporated to yield title product; 4.31 g, tlc $R_f$ 0.28 (3:1 benzene:ethyl acetate); pnmr/CDCl$_3$/TMS/delta (ppm) 1.22 (s, 3H), 1.52 (s, 3H), 3.53 (m, 2H), 5.05 (s, 2H), 5.27 (s, 2H), 7.47 (s, 10H).

PREPARATION 6

Pivaloyloxymethyl 6-alpha-Bromopenicillanate 1,1-Dioxide 6-alpha-Bromopenicillanic acid 1,1-dioxide (30 g, 0.096 mole) was dissolved in DMF (100 mL). Triethylamine (9.68 g, 0.096 mole) and chloromethyl pivalate (14.57 g, 0.096 mole) were added and the mixture stirred 1 day, then diluted with 400 mL H$_2$O and 140 mL ethyl acetate and the pH adjusted from 3.4 to 1.5 with dilute HCl. The aqueous layer was extracted 2×140 mL fresh ethyl acetate. The organic layers were combined, washed 1×100 mL saturated NaHCO$_3$, 1×100 mL H$_2$O and 1×100 mL brine and evaporated. The residual oil was triturated with hexane, taken up in CH$_2$Cl$_2$ and re-evaporated to yield title product as a solid; 10.5 g; m.p. 94°–97°; pnmr/CDCl$_3$/TMS/delta (ppm): 1.25 (s, 9H), 1.45(s, 3H), 1.62 (s, 3H), 4.57 (s, 1H), 4.85 (d, 1H, J=1.7Hz), 5.3 (d, 1H, J=1.7Hz), 6.0 (q, 2H).

PREPARATION 7

Pivaloyloxymethyl 6,6-Dibromopenicillanate 1,1-Dioxide

By the procedure of the preceding Preparation, 6,6-dibromopenicillanic acid 1,1-dioxide (98 g, 0.025 mole) was converted to present title product. The initially isolated product was further purified by chromatography on silica gel using 9:1 hexane:ethyl acetate as eluant, providing title product as a gum which solidified on standing; 25 g; pnmr/CDCl$_3$TMS/delta (ppm) 1.23 (s, 9H), 1.43 (s, 3H), 1.6 (s, 3H), 4.63 (s, 1H), 5.13 (s, 1H), 5.93 (q, 2H).

We claim:

1. A process for the preparation of a monobromo compound of the formula

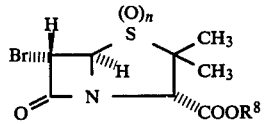

wherein n is 0, 1 or 2 and $R^8$ is hydrogen, a conventional carboxy protecting group removable by hydrogenolysis or a conventional ester forming radical which is hydrolyzable under physiological conditions, which comprises treatment of a dibromo compound of the formula

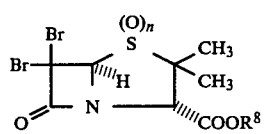

wherein n and $R^8$ are as previously defined, with substantially one molar equivalent of a bisulfite salt in a reaction-inert aqueous solvent at 0°–100° C.

2. A process of claim 1 wherein $R^8$ is hydrogen, or a group removable by hydrogenolysis which is benzyl, benzhydryl or 2-naphthylmethyl, carried out in the presence of 1–3 equivalents of sodium bicarbonate as a buffering agent, and using sodium bisulfite as the bisulfite salt at 0°–40° C.

3. The process of claim 2 wherein $R^8$ is hydrogen and n is 0.

4. The process of claim 2 wherein $R^8$ is hydrogen and n is 2.

5. The process of claim 2 wherein $R^8$ is benzyl and n is 2.

6. A process of claim 1 wherein $R^8$ is a hydrolyzable ester radical which is
gamma-butyrolacton-4-yl,
—CHR$^2$OCOR$^3$, or
—CHR$^2$OCOOR$^3$,
wherein $R^2$ is hydrogen or methyl and $R^3$ is (C$_1$–C$_6$)-alkyl using sodium bisulfite as the bisulfite salt at 0°–40° C.

7. The process of claim 6 wherein $R^8$ is pivaloyloxymethyl.

8. A process for the preparation of a desbromo compound of the formula

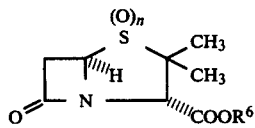

wherein n is 0, 1 or 2 and $R^6$ is hydrogen or a conventional carboxy protecting group removable by hydrogenolysis which comprises treatment of a alpha- or beta-bromo compound of the formula

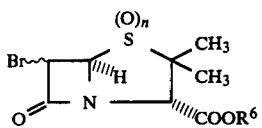

wherein n and $R^6$ is as defined previously with at least one molar equivalent of a bisulfite salt, or a dibromo compound of the formula

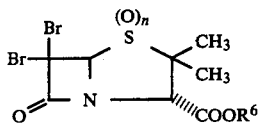

wherein n and $R^6$ is as defined previously, with at least two molar equivalents of a bisulfite salt in a reaction-inert aqueous solvent at 50°–100° C.

9. A process of claim 8 carried out in the presence of 1–3 equivalents of sodium bicarbonate as a buffering agent and using sodium bisulfite as the bisulfite salt.

10. A process of claim 9 wherein the group removable by hydrogenolysis is benzyl, benzhydryl or 2-naphthylmethyl.

11. The process of claim 9 wherein the compound treated is the dibromo compound, n is 2 and $R^6$ is hydrogen.

12. A process for the preparation of a mixture of 6-alpha and 6-beta compounds of the formula

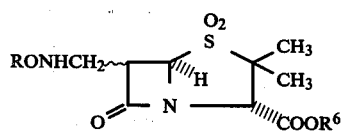

wherein R is $(C_1-C_4)$alkyl or benzyl and $R^6$ is hydrogen or a conventional carboxy protecting group removable by hydrogenolysis, which comprises treatment of a bromo compound of the formula

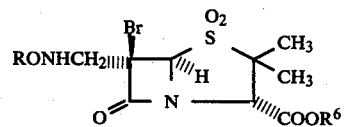

wherein R and $R^6$ are as previously defined, with at least one molar equivalent of a bisulfite salt in a reaction-inert aqueous solvent at 50°–100° C.

13. A process of claim 12 carried out in the presence of 1–3 equivalents of sodium bicarbonate as a buffering agent and using sodium bisulfite as the bisulfite salt.

14. A process of claim 13 wherein the group removable by hydrogenolysis is benzyl, benzhydryl or 2-naphthylmethyl.

15. The process of claim 14 wherein $R^6$ is benzyl and R is ethyl.

* * * * *